United States Patent [19]

Vancheri et al.

[11] 4,092,123
[45] May 30, 1978

[54] DUAL PURPOSE PERSONAL DOSIMETER

[75] Inventors: Frank J. Vancheri; Stanley P. Nebash, both of Pittsburgh; Paul W. McConnaughey, Wilkinsburg, all of Pa.

[73] Assignee: Mine Safety Appliances Company, Pittsburgh, Pa.

[21] Appl. No.: 822,396

[22] Filed: Aug. 8, 1977

[51] Int. Cl.² ............................................. G01N 1/00
[52] U.S. Cl. ................................................ 23/254 R
[58] Field of Search ............ 23/254 R, 255 R, 232 R; 128/2 C; 73/421.5 R

[56] References Cited

U.S. PATENT DOCUMENTS

| 2,823,985 | 2/1958 | Strange | 23/232 R X |
| 3,276,241 | 10/1966 | Hübner | 23/255 R |
| 3,539,302 | 11/1970 | Dreckmann | 23/232 R |
| 3,681,027 | 8/1972 | Smith | 23/232 R |
| 3,868,222 | 2/1975 | Barringer | 23/254 R X |

Primary Examiner—Robert M. Reese
Attorney, Agent, or Firm—Brown, Flick & Peckham

[57] ABSTRACT

A gas sampler in the form of a bubbler is associated with a transparent detector tube containing a chemical that changes color when a toxic gas flows through it. Conduit means connect the air outlets of the two devices with the inlet of a suction pump to draw air through the bubbler and tube simultaneously. The flow of air from the bubbler to the pump is restricted relative to the flow from the tube to the pump.

5 Claims, 1 Drawing Figure

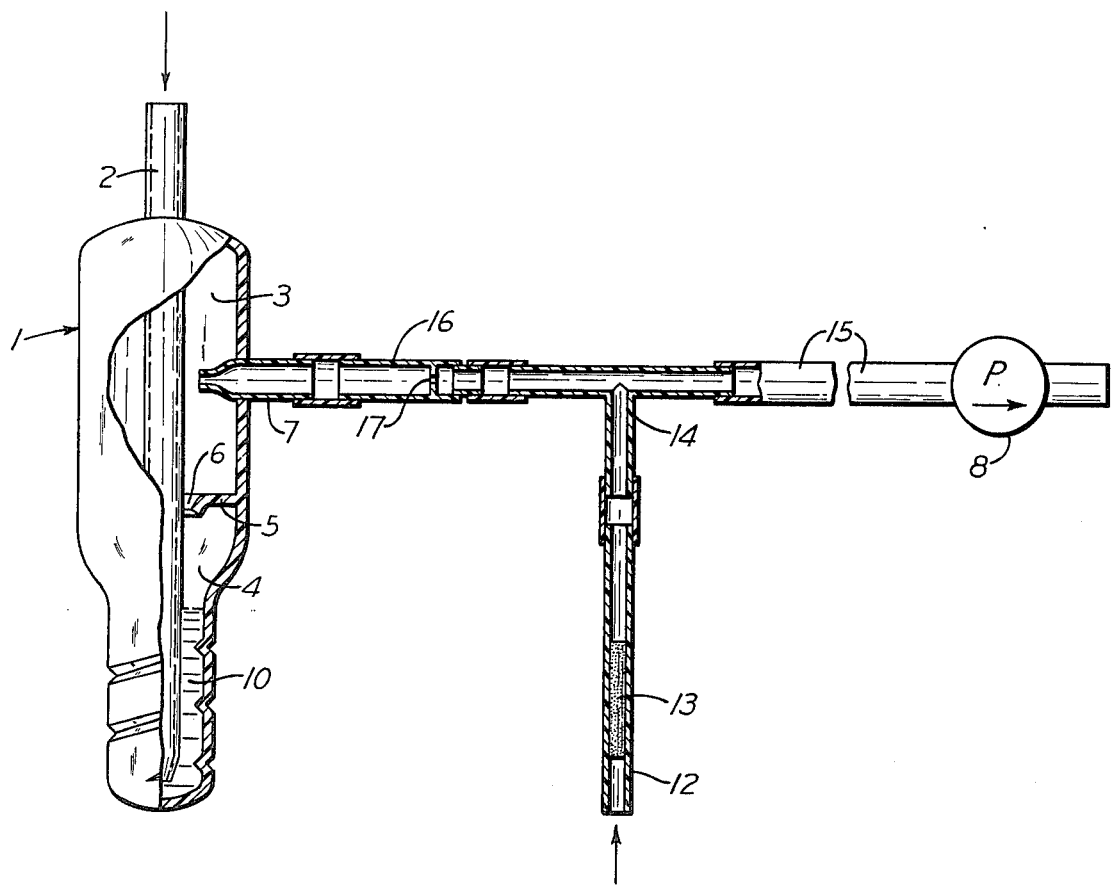

DUAL PURPOSE PERSONAL DOSIMETER

For people who work in an atmosphere that is likely to be toxic, government regulations require sampling of the air periodically. For example, the permissible level of exposure to a toxic gas over an 8 hour shift is determined and then sampling of the air over a period of at least 7½ hours is required to make sure that the average concentration of toxic gas is below the permitted level, known as the threshhold limit value. In addition, a person may suspect that he is suddenly being exposed to a greater concentration, possibly being warned by a leak or other equipment failure, by smell or by noting symptoms of exposure in himself or co-workers.

It is among the objects of this invention to provide a simple wearable dosimeter which will provide both long term gas sampling and on the spot emergency sampling, and which will not be affected by the position of the body of the user.

The preferred embodiment of the invention is illustrated in the accompanying drawing, in which the single FIGURE is a side view of the dosimeter, with parts broken away in vertical section.

The dual purpose dosimeter disclosed in the drawing includes two gas samplers that utilize two different sorbent techniques and a single pump. One sampler is a bubbler and the other is a colorimetric detector tube. The bubbler itself is the subject matter of our copending patent application, Ser. No. 817,365, filed July 20, 1977. As described in that application, the bubbler includes a normally upright bottle 1, preferably made of glass or transparent plastic. The lower portion of the bottle most suitably has a smaller diameter than the upper portion. Extending from near the bottom of the bottle up through the top there is a central inlet tube 2. It is sealed in the top of the bottle, by which it is supported. The bottle is divided into upper and lower chambers 3 and 4 by means of a collar 5 that encircles the inlet tube in the lower part of the larger upper portion of the bottle and is sealed to the side of the bottle. The opening through the collar is slightly larger than the tube so that there is clearance between them to provide a passage 6 between the two chambers. Although the collar can be flat, it is preferred to provide it with a slight downturned lip. An exhaust tube 7 is sealed in the side of the upper chamber 3, with the inner end of the tube near one side of the central inlet tube. The outer end of the exhaust tube is connected by a conduit to a battery-operated miniature suction pump 8 for drawing a gas, such as contaminated air, for example, down through the inlet tube and out of its lower end. The pump is a standard item.

The lower chamber 4 of the bubbler contains a predetermined volume of a sorbent solution 10, through which it is desired that the contaminated gas should bubble. The liquid may be water or any other suitable sorbent. Its depth will depend upon the gas being treated, which can be any gas containing a pollutant that can be adsorbed in a liquid sorbent. The gas drawn through the bubbler may be, for example, air contaminated with anti-cholinesterase inhibitors such as phosphate and phosphate ester pesticides that may be present in low concentrations. A weak sulfuric acid solution, pH about 3, is appropriate for determining phosphate and phosphate ester pesticides. Or, the bubbler may detect other gases, more particularly acid gases such as HGN or sulphuric acid vapors or bases such as sodium hydroxide or ammonia, or organic vapors such as benzene acrylonitril or vinyl chloride, which can be absorbed in appropriate bubbler solutions and measured with an appropriate detector tube. The contaminated air bubbles up through the liquid, which removes the contaminants.

The capacity of the lower chamber 4 of the bubbler is such that when the bubbler is turned on its side, most of the liquid will remain in the lower chamber and all of it will be beneath the inlet tube 2. A small amount of the liquid may pass through the central passage 6 and into the upper chamber. In this position all of the liquid is beneath the outlet of the inlet tube and below the inlet of the exhaust tube 7.

Even though the bottle is inverted, the capacity of the upper chamber 3 is such that all of the liquid in that chamber will be below the exhaust tube and, of course, below the outlet of the inlet tube. If the bottle is then turned back on its side, the upper level of the liquid in the upper chamber will still remain below the inlet of the exhaust tube. Consequently, no matter what position the bottle is in, none of the liquid will escape through the inlet tube or the exhaust tube. The bubbler is intended to be attached to the clothing of a worker, but since the bubbler is spill-proof, it continues to function regardless of the motions or positions of the worker. Even though he bends over, twists or lies on his back, the liquid in the bubbler will not escape.

The colorimetric detector tube consists of a transparent tube containing a chemical 13 that will change color in accordance with the toxic gas in the air flowing through the tube. The length of the discoloration will depend on the toxic gas in the air passing through the tube. In some cases the color is developed by adding a solution to the chemical 13; for example, a suitable detector tube for determining phosphate and phosphate ester pesticides contains 4-(p-nitrobenzoyl) pyridine on an inert granular carrier and is developed by treatment with an aqueous solution of p-amino-o-ethoxy-o-sulfodiphenylamine and sodium pyrophosphate. The upper end of the tube is connected to the lower end of the stem of a tubular T coupling 14. One end of the cross bar of the T is connected by a flexible tube 15 to the suction pump, while the other end of the cross bar is suitably connected to one end of a short rigid tube 16 provided internally with a transverse wall having a central orifice 17 in it. This tube is connected to exhaust tube 7 of the bubbler.

When this dosimeter, mounted on a suitable support, is worn by a man during a working shift, the pump draws air through the bubbler continuously. At the end of the shift, the bubbler is turned in to a laboratory where the contents of the bubbler are analyzed to determine whether the threshhold limit value in the working area was exceeded during the shift. Before that, while the man is still working, he may notice that the chemical in the colorimetric tube is changing color, or he may be warned by some abnormal condition that there may be an increase in the toxic gas so that he will look at the tube to see whether the chemical is changing color. He then can compare the length of the color change with a calibration curve on a chart to learn the toxic gas concentration at that time. If it is a dangerous concentration, he can leave the area.

The flow through the bubbler and detector tube is regulated by obtaining the proper balance between the pressure drop in the detector tube, the solution level in the bubbler, and the size of orifice 17. This balance can be adjusted to some degree. A preferred flow ratio is 30 cc/min. through the bubbler and 150 cc/min. through the detector tube.

The personal dosimeter disclosed herein is designed to accommodate simultaneously both low and high concentrations of pollutants in the atmosphere. The bubbler does long-term sampling (8 hours) at low flow and accommodates low concentrations of toxic gas, whereas the detector tube will indicate higher concentrations obtained in relatively short exposures (1 to 60 minutes).

According to the provisions of the patent statutes, we have explained the principle of our invention and have illustrated and described what we now consider to represent its best embodiment. However, we desire to have it understood that, within the scope of the appended claims, the invention may be practiced otherwise than as specifically illustrated and described.

We claim:

1. A dual purpose personal dosimeter comprising a bubbler provided with an inlet for contaminated air and with an air outlet, a transparent detector tube provided with an inlet for contaminated air and with an air outlet, a chemical in said tube that changes color when certain contaminants in air flow through it, a suction pump provided with an inlet, conduit means connecting said air outlets with the pump inlet to draw contaminated air into said bubbler and tube simultaneously, and means for restricting flow of air from the bubbler to the pump relative to the flow from the tube to the pump.

2. A dual purpose personal dosimeter according to claim 1, in which said flow restricting means is disposed in said conduit means connecting said bubbler outlet with said pump.

3. A dual purpose personal dosimeter according to claim 1, in which said conduit means include a separate conduit connected to each of said air outlets and a third conduit connecting both of said separate conduits to the pump inlet, and said flow restricting means is an orifice member mounted in the separate conduit connected to the bubbler outlet.

4. A dual purpose personal dosimeter according to claim 1, in which said flow restricting means reduces the rate of flow from the bubbler to approximately one-fifth the rate of flow from said tube.

5. A dual purpose personal dosimeter according to claim 1, in which said bubbler includes a normally upright bottle, a central inlet tube extending from near the bottom of the bottle up through the top of the bottle, and a liquid in the lower part of the bottle surrounding the lower end portion of said inlet tube, said bubbler air outlet being in the side of the upper part of the bottle.

* * * * *